United States Patent
Yoneya (10) Patent No.: US 12,029,491 B2
(45) Date of Patent: Jul. 9, 2024

(54) EYE INFORMATION ESTIMATE APPARATUS, EYE INFORMATION ESTIMATE METHOD, AND PROGRAM

(71) Applicant: NIPPON TELEGRAPH AND TELEPHONE CORPORATION, Tokyo (JP)

(72) Inventor: Makoto Yoneya, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 668 days.

(21) Appl. No.: 17/291,585

(22) PCT Filed: Oct. 25, 2019

(86) PCT No.: PCT/JP2019/041822
§ 371 (c)(1),
(2) Date: May 5, 2021

(87) PCT Pub. No.: WO2020/095708
PCT Pub. Date: May 14, 2020

(65) Prior Publication Data
US 2021/0393125 A1    Dec. 23, 2021

(30) Foreign Application Priority Data
Nov. 8, 2018    (JP) ................. 2018-210346

(51) Int. Cl.
*A61B 3/14*    (2006.01)
*A61B 3/113*    (2006.01)

(52) U.S. Cl.
CPC ............ *A61B 3/14* (2013.01); *A61B 3/113* (2013.01)

(58) Field of Classification Search
CPC ......... A61B 3/113; A61B 3/0025; A61B 3/14; A61B 3/112; A61B 5/6803; A61B 3/09;
(Continued)

(56) References Cited

U.S. PATENT DOCUMENTS

| 2011/0150334 A1* | 6/2011 | Du | G06V 40/19 |
| | | | 382/173 |
| 2016/0335475 A1* | 11/2016 | Krenzer | G06V 40/20 |

(Continued)

OTHER PUBLICATIONS

Tobii pro (2018) "The eyes are as eloquent as the mouth" [online] Accessed on Jun. 6, 2018, website: https://www.tobiipro.com/ja/?gclid=EAlaIQobChMI9dzRgfq92wIV1YePCh2I1ge6EAAYASAAEgLqy_D_BwE.

*Primary Examiner* — Ajibola A Akinyemi (57) ABSTRACT

To provide a technique for estimating, using an image photographed by a camera with a low sampling frequency, information on a position and a size of a pupil or an iris in time units that are finer than the actual sampling frequency. An eye information estimation apparatus includes: a profile determination information acquiring unit which acquires, from an image obtained by photographing an eye of a person who is a subject, coordinates of two points P1 and P2 corresponding to a limbus of a pupil or an iris of a prescribed row included in the image and, when a shape of the pupil or the iris is assumed to be an ellipse, a length of a major axis of the ellipse and eye rotation center coordinates of a three-dimensional eye rotation system that constrains the pupil or the iris; and an eye information calculating unit which calculates an ellipse profile including center coordinates and a deflection angle of the ellipse that represent a position of the pupil or the iris and a length of a major axis and a length of a minor axis of the ellipse that represent a size of the pupil or the iris from the coordinates of the points
(Continued)

P1 and P2, tangent slopes of the ellipse at the points P1 and P2, the length of the major axis, the eye rotation center coordinates, and an eye rotation radius of the three-dimensional eye rotation system.

20 Claims, 7 Drawing Sheets

(58) Field of Classification Search
CPC ......... A61B 3/111; A61B 3/145; A61B 5/163; A61B 5/291; A61B 2562/0219; A61B 5/11; A61B 5/1114; A61B 5/316; A61B 3/0091
USPC ........................................................ 382/128
See application file for complete search history.

(56) References Cited

U.S. PATENT DOCUMENTS

2018/0003963 A1* 1/2018 Benitez .................. G02B 30/24
2021/0149212 A1* 5/2021 Benítez .................. G02B 30/10

* cited by examiner

EYE INFORMATION ESTIMATE APPARATUS, EYE INFORMATION ESTIMATE METHOD, AND PROGRAM

CROSS-REFERENCE TO RELATED APPLICATIONS

This application is a U.S. 371 Application of International Patent Application No. PCT/JP2019/041822, filed on 25 Oct. 2019, which application claims priority to and the benefit of JP Application No. 2018-210346, filed on 08 Nov. 2018, the disclosures of which are hereby incorporated herein by reference in their entireties.

TECHNICAL FIELD

The present invention relates to a technique for estimating information on a position and a size of a pupil or an iris.

BACKGROUND ART

According to reference patent literature 1, a feature amount based on a dynamic change in an eye of a person who is a subject can be extracted and the person's musical preference can be estimated in real time based on the extracted feature amount (reference patent literature 1). (Reference patent literature 1: Japanese Patent Application Laid-open No. 2015-131069)

For example, a dedicated apparatus (NPL 1) called an eye movement measuring instrument can be used to estimate the dynamic change in the eye which is used in reference patent literature 1.

CITATION LIST

Non Patent Literature

[NPL1] tobii pro, [online], [retrieved on Jun. 6, 2018], the Internet <URL:https://www.tobiipro.com/ja/?gclid=EAIaIQobChMI9dzRgfq92wIVlYePCh2llge6EAAYASAAEgLqy_D_BwE>

SUMMARY OF THE INVENTION

Technical Problem

According to reference patent literature 1, using a feature amount based on a dynamic change in a person's eye enables a musical preference to be estimated in real time. However, since calculating a feature amount related to a dynamic change in an eye such as a damping coefficient or a natural angular frequency of a microsaccade used in reference patent literature 1 requires that a fine eye position change in the order of milliseconds be accurately captured, an eye movement measuring instrument capable of photographing an image at an extremely high sampling frequency such as 1,000 Hz must be used. Therefore, for example, when a camera with relatively low performance (for example, a camera with a low sampling frequency such as 15 to 60 Hz) which is built into a smartphone or a personal computer is used, since an insufficient sampling frequency prevents a fine eye position change in the order of milliseconds from being accurately acquired and prevents a feature amount related to a dynamic change in an eye such as a damping coefficient or a natural angular frequency of a microsaccade from being calculated, there is a problem in that a musical preference cannot be estimated.

In consideration thereof, an object of the present invention is to provide a technique for estimating, using an image photographed by a camera with a low sampling frequency, information on a position and a size of a pupil or an iris in extremely fine time units that are finer than an actual sampling frequency.

Means for Solving the Problem

An aspect of the present invention includes: a profile determination information acquiring unit which acquires, from an image obtained by photographing an eye of a person who is a subject, coordinates $(x_1, y_0)$ and $(x_2, y_0)$ of two points P1 and P2 corresponding to a limbus of a pupil or an iris of a prescribed row included in the image and, when a shape of the pupil or the iris is assumed to be an ellipse, a length R of a major axis of the ellipse and eye rotation center coordinates $(x_e, y_e)$ of a three-dimensional eye rotation system that constrains the pupil or the iris; and an eye information calculating unit which calculates, when $\theta_1$ and $\theta_2$ denote tangent slopes of the ellipse at the point P1 and the point P2 and $R_e$ denotes an eye rotation radius of the three-dimensional eye rotation system, an ellipse profile including center coordinates $(x_c, y_c)$ and a deflection angle $\varphi$ of the ellipse that represent a position of the pupil or the iris and a length $R_a$ of a major axis and a length $R_b$ of a minor axis of the ellipse that represent a size of the pupil or the iris from the coordinates $(x_1, y_0)$ and $(x_2, y_0)$ of the points P1 and P2, the tangent slopes $\theta_1$ and $\theta_2$, the length R of the major axis, the eye rotation center coordinates $(x_e, y_e)$, and the eye rotation radius $R_e$.

Effects of the Invention

According to the present invention, information on a position and a size of a pupil or an iris can be estimated, using an image photographed by a camera with a low sampling frequency, in extremely fine time units that are finer than the actual sampling frequency.

DESCRIPTION OF EMBODIMENTS

An embodiment of the present invention will be described in detail below. It should be noted that a constituent unit having a same function will be denoted by a same numeral and a redundant description will be omitted.

TECHNICAL BACKGROUND

A pupil or an iris is assumed as a subject for which information on a position and a size is to be estimated. In addition, an image obtained by photographing an eye of a person who is a subject is used to estimate the position and the size of the pupil or the iris. During the estimation, it is assumed that a shape of the pupil or the iris in the photographed image is an ellipse. Therefore, the position and the size of the pupil or the iris are to be estimated as center coordinates and a deflection angle of the ellipse and a length of a major axis and a length of a minor axis of the ellipse. Specifically, from coordinates of two points P1 and P2 that correspond to a limbus of a pupil or an iris of a prescribed row included in an image obtained by photographing an eye of a person who is a subject, the center coordinates, the deflection angle, the length of a major axis, and the length of a minor axis which constitute a profile of the ellipse are estimated. In doing so, it is assumed that the length of the major axis does not change when the image is being photographed at a prescribed sampling frequency. Hereinafter, this length will be denoted by R.

As described above, a problem of estimating the position and the size of a pupil or an iris boils down to a problem of obtaining center coordinates $(x_c, y_c)$, a deflection angle $\varphi$, a length $R_a$ of a major axis, and a length $R_b$ of a minor axis of an ellipse from coordinates $(x_1, y_0)$ and $(x_2, y_0)$ of points P1 and P2 on an ellipse, tangent slopes $\theta_1$ and $\theta_2$ of the ellipse at the two points, and a length R of the major axis of the ellipse (provided that $R_a = R$).

A method of obtaining the coordinates $(x_1, y_0)$ and $(x_2, y_0)$ of points P1 and P2, the tangent slopes $\theta_1$ and $\theta_2$ of the ellipse at the two points, and the length R of the major axis of the ellipse from an image obtained by photographing an eye of a person who is a subject will be described later.

Hereinafter, a procedure for solving the problem described above will be explained. Generally, an ellipse at an arbitrary position on a two-dimensional plane is represented by the following equation.

[Formula 1]

$$\left(\frac{(x-x_c)\cos\psi + (y-y_c)\sin\psi}{R_a}\right)^2 + \left(\frac{-(x-x_c)\sin\psi + (y-y_c)\cos\psi}{R_b}\right)^2 = 1$$

Now, in order to solve the problem described above, coordinate transformation is performed so that the ellipse at the arbitrary position corresponds to an ellipse which passes a point (1, 0) on an x-axis and a point (0, 1) on a y-axis and which comes into contact with the x-axis at the point (1, 0) and comes into contact with the y-axis at the point (0, 1), and calculation is performed using the fact that the ellipse after the transformation is represented by the following equation.

[Formula 2]

$$(x-1)^2 + (y-1)^2 + 2\alpha xy = 1 \quad (|\alpha| \leq 1)$$

In this case, a is referred to as a hyperparameter.

A detailed description will now be given. Coordinates $(x_s, y_s)$ of an intersection C of a tangent of the ellipse at the point P1 and a tangent of the ellipse at the point P2 is represented by the following equation using coordinates $(x_1, y_0)$ and $(x_2, y_0)$ of the points P1 and P2 and tangent slopes $\theta_1$ and $\theta_2$ of the ellipse at the two points.

[Formula 3]

$$\begin{pmatrix} x_s \\ y_s \end{pmatrix} = \begin{pmatrix} \dfrac{x_1 \tan\theta_1 - x_2 \tan\theta_2}{\tan\theta_1 - \tan\theta_2} \\ y_0 + \dfrac{(x_1 - x_2)\tan\theta_1 \tan\theta_2}{\tan\theta_1 - \tan\theta_2} \end{pmatrix} \quad (1)$$

Assuming that

[Formula 4]

$$\vec{q}_1 = \begin{pmatrix} \dfrac{1}{x_1 - x_2} \\ \dfrac{1}{(x_1 - x_2)\tan\theta_2} \end{pmatrix}$$

$$\vec{q}_2 = \begin{pmatrix} \dfrac{-1}{x_1 - x_2} \\ \dfrac{1}{(x_1 - x_2)\tan\theta_1} \end{pmatrix}$$

$$\vec{x} = \begin{pmatrix} x \\ y \end{pmatrix}$$

are satisfied, an equation representing an ellipse obtaining by transforming coordinate systems such that the intersection C corresponds to a point (0, 0), the point P1 corresponds to a point (1, 0), and the point P2 corresponds to a point (0, 1) can be represented as follows.

[Formula 5]

$$(\vec{q}_1 \cdot \vec{x} - 1)^2 + (\vec{q}_2 \cdot \vec{x} - 1)^2 + 2\alpha(\vec{q}_1 \cdot \vec{x})(\vec{q}_2 \cdot \vec{x}) = 1$$

Consequently, a profile of the ellipse or, in other words, center coordinates $(x_c, y_c)$, a deflection angle $\varphi$, a length $R_a$ of a major axis, and a length $R_b$ of a minor axis of the ellipse can be expressed using the hyperparameter $\alpha$ as follows.

[Formula 6]

$$x_c = \frac{(x_1 - x_s) + (x_2 - x_s)}{\alpha + 1} + x_s \quad (2a)$$

$$y_c = \frac{2(y_0 - y_s)}{\alpha + 1} + y_s \quad (2b)$$

$$\psi = -\frac{1}{2}\arctan\left(\frac{\lambda_1 + \lambda_2}{1 - \lambda_1\lambda_2 + \dfrac{(\lambda_1 - \lambda_2)^2}{2(\alpha - 1)}}\right) \quad (3)$$

$$R_{a,b}^2 = \left(\frac{y_0 - y_s}{\alpha + 1}\right)^2 \quad (4)$$

$$\left\{\frac{f_1 + f_2}{2} - \alpha f_0 \pm \left\{(f_1\alpha - f_0)(f_2\alpha - f_0) + \left(\frac{f_1 - f_2}{2}\right)^2\right\}\right\}$$

where

[Formula 7]

$$x_s = \frac{x_1 \tan\theta_1 - x_2 \tan\theta_2}{\tan\theta_1 - \tan\theta_2} \quad (5a)$$

$$y_s = y_0 \frac{(x_1 - x_2)\tan\theta_1 \tan\theta_2}{\tan\theta_1 - \tan\theta_2} \quad (5b)$$

$$\lambda_1 = \frac{x_1 - x_s}{y_0 - y_s}\left(= \frac{1}{\tan\theta_1}\right) \quad (6a)$$

$$\lambda_2 = \frac{x_2 - x_s}{y_0 - y_s}\left(= \frac{1}{\tan\theta_2}\right) \quad (6b)$$

-continued $$f_0 = 1 + \lambda_1\lambda_2 \quad (7a)$$

$$f_1 = 1 + \lambda_1^2 \quad (7b)$$

$$f_2 = 1 + \lambda_2^2. \quad (7c)$$

In this case, $R_{a,b}^2$ in Equation (4) signifies either $R_a^2$ or $R_b^2$ and signifies that a smaller of the values (in other words, two values expressed using ±) on a right side of Equation (4) is $R_b^2$ and a larger of the values is $R_a^2$. In addition, a square root of the right side of Equation (4) is $R_a$, $R_b$.

A ratio r ($=R_b/R_a$) of the length of the minor axis to the length of the major axis can also be expressed using the hyperparameter α as follows.

[Formula 8]

$$r^2 = \frac{1-\alpha^2}{(1+\alpha)^4} \cdot \frac{(y_0-y_s)^2(x_1-x_2)^2}{R_a^4} \quad (8)$$

Hereinafter, Equation (2a) and Equation (2b) will be referred to as expressions of the center coordinates ($x_c$, $y_c$) using the hyperparameter α. In a similar manner, Equation (3) will be referred to as an expression of the deflection angle φ using the hyperparameter α, Equation (4) will be referred to as an expression of the length $R_a$ of the major axis using the hyperparameter α and an expression of the length $R_b$ of the minor axis using the hyperparameter α, and Equation (8) will be referred to as an expression of the ratio r of the length of the minor axis to the length of the major axis using the hyperparameter α. In addition, the hyperparameter α is also referred to as a hyperparameter that is used in expressions of the ellipse profile.

Therefore, using the expressions presented above, by obtaining the hyperparameter α (where |α|≤1) that satisfies $R_a=R$ using Equation (4), the center coordinates ($x_c$, $y_c$), the deflection angle φ, and the length $R_b$ of the minor axis can be obtained.

A method of obtaining the coordinates ($x_1$, $y_0$) and ($x_2$, $y_0$) of points P1 and P2, the tangent slopes $\theta_1$ and $\theta_2$ of the ellipse at the two points, and the length R of the major axis of the ellipse from an image obtained by photographing an eye of a person who is a subject will now be described.

The coordinates ($x_1$, $y_0$) and ($x_2$, $y_0$) of points P1 and P2 can be acquired by detecting a region and boundary of the pupil or the iris using, for example, a method described in reference non patent literature 1.

(Reference non patent literature 1: Daugman, J, "Probing the uniqueness and randomness of IrisCodes: Results from 200 billion iris pair comparisons", Proceedings of the IEEE, Vol. 94, No. 11, pp. 1927-1935, 2006.)

In addition, the tangent slopes $\theta_1$ and $\theta_2$ of the ellipse at the points P1 and P2 can be acquired using coordinates of points corresponding to a limbus of a pupil or an iris of a row adjacent to the prescribed row and the coordinates ($x_1$, $y_0$) and ($x_2$, $y_0$) of the points P1 and P2. Specifically, the tangent slopes $\theta_1$ and $\theta_2$ are obtained as follows. First, denoting coordinates of two points P1' and P2' corresponding to a limbus of a pupil or an iris of a row positioned on an upper side in the image among the rows adjacent to the prescribed row as ($x_1'$, $y_0'$) and ($x_2'$, $y_0'$), slopes $\theta_1'$ and $\theta_2'$ are obtained by the following equations (refer to FIG. 1).

Figure 1:
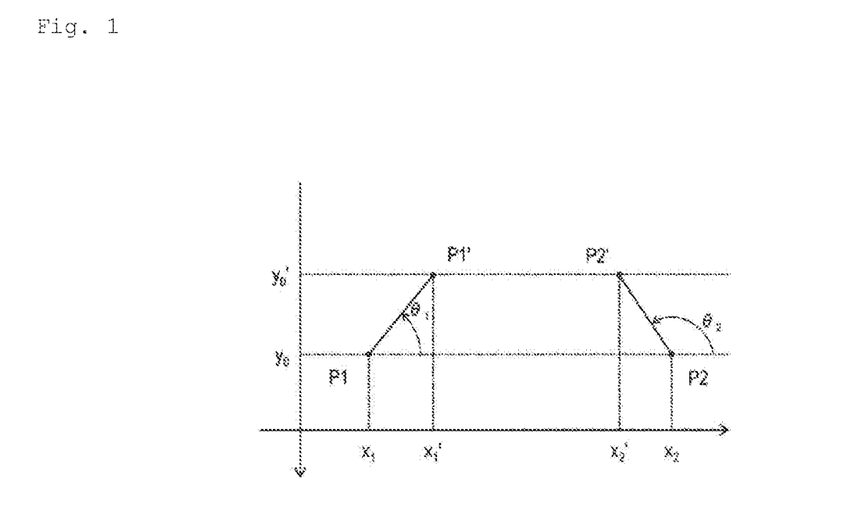
FIG. 1 is a diagram showing an example of four points corresponding to limbi of pupils (irises) of two adjacent rows.

[Formula 9]

$$\theta_1' = \arctan\frac{y_0'-y_0}{x_1'-x_1}$$

$$\theta_2' = \arctan\frac{y_0'-y_0}{x_2'-x_2}$$

In a similar manner, denoting coordinates of two points P1" and P2" corresponding to a limbus of a pupil or an iris of a row positioned on a lower side in the image among the rows adjacent to the prescribed row as ($x_1''$, $y_0''$) and ($x_2''$, $y_0''$), slopes $\theta_1''$ and $\theta_2''$ are obtained by the following equations.

[Formula 10]

$$\theta_1'' = \arctan\frac{y_0''-y_0}{x_1''-x_1}$$

$$\theta_2'' = \arctan\frac{y_0''-y_0}{x_2''-x_2}$$

Subsequently, slopes $\theta_1$ and $\theta_2$ are obtained by the following equations using the slopes $\theta_1'$, $\theta_2'$, $\theta_1''$, and $\theta_2''$.

[Formula 11]

$$\theta_1 = \frac{\theta_1' + \theta_1''}{2}$$

$$\theta_2 = \frac{\theta_2' + \theta_2''}{2}$$

In other words, the slopes $\theta_1$ and $\theta_2$ are obtained as average values of the two slopes described below. The first is a slope calculated using coordinates of two points corresponding to a limbus of a pupil or an iris of a row positioned on an upper side in the image among the rows adjacent to the prescribed row and the coordinates ($x_1$, $y_0$) and ($x_2$, $y_0$) of the points P1 and P2. The second is a slope calculated using coordinates of two points corresponding to a limbus of a pupil or an iris of a row positioned on a lower side in the image among the rows adjacent to the prescribed row and the coordinates ($x_1$, $y_0$) and ($x_2$, $y_0$) of the points P1 and P2.

As the length R of the major axis of the ellipse, for example, a length of a major axis obtained as a result of performing ellipse fitting with respect to a limbus of a pupil or an iris included in the image may be used.

The above description shows that the problem described above can be solved. However, using the method described above as a method of obtaining the tangent slopes $\theta_1$ and $\theta_2$ of the ellipse at points P1 and P2 may sometimes result in lowering estimation accuracy. This is because, due to movements of the eye being extremely high speed, photographing the eye using a camera with a relatively low sampling frequency such as a camera of a smartphone results in a distorted photograph of the eye. An occurrence of graphical distortion due to a deviation in an exposure timing for each scanning row when photographing a subject that is moving at high speed using a camera with a relatively low sampling frequency is referred to as a rolling shutter effect.

In consideration thereof, in order to determine the tangent slopes $\theta_1$ and $\theta_2$ of the ellipse at points P1 and P2 at higher accuracy, a method described below may be used. This method involves imposing a new constraint. Hereinafter, the constraint to be newly imposed and an algorithm for calculating an ellipse profile based on the constraint and assuming that a tangent slope is unknown will be described.

(Constraint: Three-Dimensional Eye Rotation System)

Figure 2:
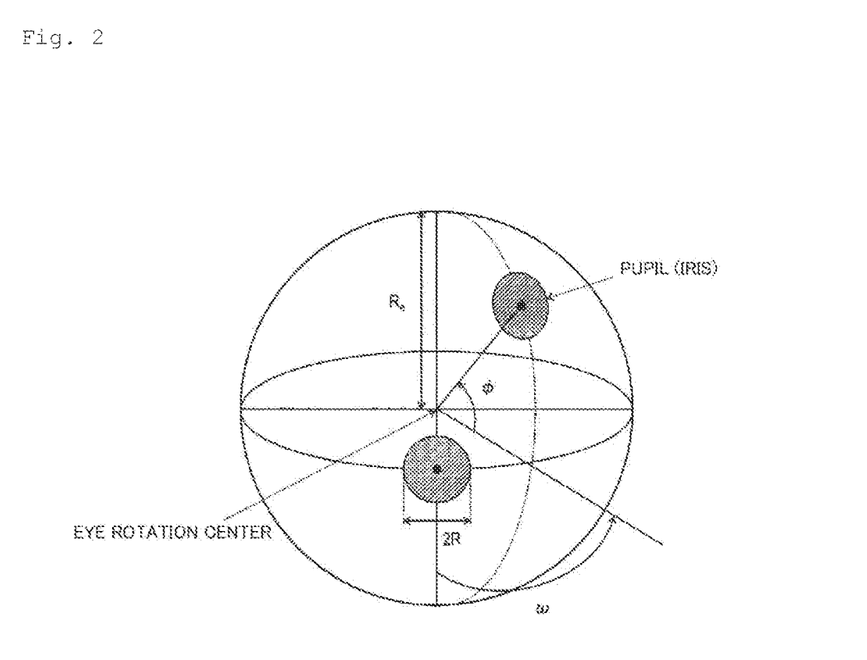
FIG. 2 is a diagram showing a three-dimensional eye rotation system.

It is assumed that shapes of the pupil and the iris are disks, a shape of an eye is a true sphere, and the pupil and the iris move while being constrained to a surface of the eye (refer to FIG. 2). In other words, it is assumed that an ellipse obtained by photographing the pupil or the iris is a result of the disk rotating on the true sphere. It should be noted that, in FIG. 2, a hatched circle represents a pupil or an iris, and a sphere with a radius of $R_e$ represents an eye. Hereinafter, a system in which the pupil or the iris performs rotational movement while being constrained to the surface of the eye will be referred to as a three-dimensional eye rotation system.

In an image obtained by photographing an eye of a person who is a subject, let $(x_e, y_e)$ denote eye rotation center coordinates of a three-dimensional eye rotation system, $R_e$ denote an eye rotation radius of the three-dimensional eye rotation system, R denote a pupil radius (an iris radius), w denote a pupil central longitude (an iris central longitude), and $\phi$ denote a pupil central latitude (an iris central latitude). Consequently, center coordinates, a deflection angle, a length of a major axis, and a length of a minor axis which constitute an ellipse profile (in other words, a position and a size of the pupil (iris)) are represented by the following equations (refer to FIGS. 2 and 3).

Figure 3:
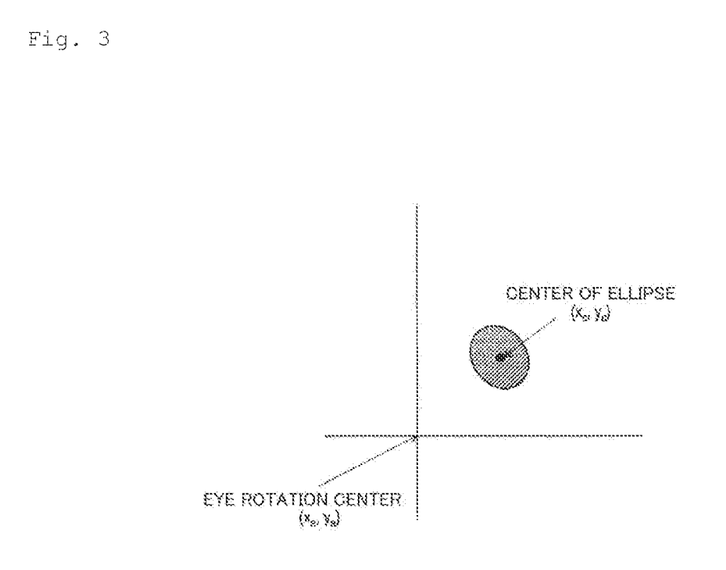
FIG. 3 is a diagram showing an example of a positional relationship between an eye rotation center and a center of an ellipse.

[Formula 12]

$$x_c = x_e + R_e \cos\varphi \sin\omega$$

$$y_c = y_e + R_e \sin\varphi$$

$$\psi = \arctan\frac{\tan\varphi}{\sin\omega}$$

$$R_a = R$$

$$R_\theta = R\cos\varphi\cos\omega$$

In addition, based on the assumption of a three-dimensional eye rotation system, a relational expression to satisfy the following two equations is derived.

[Formula 13]

$$\tilde{X}^2 + \tilde{Y}^2 = 1 - r^2 \quad (9a)$$

$$\frac{\tilde{Y}^2}{\tilde{X}^2} = \tan^2\psi. \quad (9b)$$

where

[Formula 14]

$$\tilde{X}^2 = \left(\frac{x_c + x_e}{R_e}\right)^2 \quad (10a)$$

$$\tilde{Y}^2 = \left(\frac{y_c + y_e}{R_e}\right)^2. \quad (10b)$$

(Ellipse Profile Calculation Algorithm)

The ellipse profile calculation algorithm assumes that the eye rotation center coordinates $(x_e, y_e)$ and the eye rotation radius $R_e$ have been provided in advance. The eye rotation center coordinates $(x_e, y_e)$ are determined at a time point of photography of an eye of a person who is a subject and can be obtained from an image obtained by photographing the eye of the person who is a subject. A method of obtaining the eye rotation center coordinates $(x_e, y_e)$ (an eye rotation center coordinate calculation algorithm) will be described later. On the other hand, the eye rotation radius $R_e$ is not determined at the time point of photography of an eye of a person who is a subject and conceivably takes a constant value during a certain period prior to photography. Therefore, a size of the eye (in other words, the eye rotation radius $R_e$) may be obtained prior to photography by a separate method such as taking a measurement with a prescribed measuring instrument.

Hereinafter, the ellipse profile calculation algorithm will be described.

<<Ellipse Profile Calculation Algorithm>>

Step 1: Provide suitable initial values as tangent slopes $\theta_1$ and $\theta_2$ of the ellipse at two points P1 and P2. For example, the tangent slopes $\theta_1$ and $\theta_2$ obtained by the method described above may be used as the initial values.

Step 2: Obtain coordinates $(x_s, y_s)$ of an intersection C of a tangent of the ellipse at the point P1 and a tangent of the ellipse at the point P2. Specifically, the coordinates $(x_s, y_s)$ are obtained by Equation (1).

Step 3: Using Equation (4), obtain the hyperparameter $\alpha$ (where $|\alpha| \leq 1$) that satisfies $R_a = R$.

Step 4: Using the hyperparameter $\alpha$ obtained in step 3, obtain the deflection angle $\phi$ and a square $r^2$ of the ratio r of the length of the minor axis to the length of the major axis according to Equations (3) and (8). In addition, calculate the center coordinates $(x_c, y_c)$ according to Equations (2a) and (2b).

Step 5: Calculate a non-negative cost function Cost defined by the following equations using the deflection angle $\varphi$, the square $r^2$ of the ratio r, and the center coordinates $(x_c, y_c)$ obtained in step 4.

[Formula 15]

$$Cost = C_1^2 + C_2^2 \quad (11)$$

$$C_1 = \tilde{X}^2 + \tilde{Y}^2 - 1 + r^2 \quad (12a)$$

$$C_2 = \tilde{Y}^2 - \tilde{X}^2 \tan^2\psi \quad (12b)$$

Equations (12a) and (12b) are cost functions respectively derived from Equations (9a) and (9b). When the tangent slopes $\theta_1$ and $\theta_2$ take correct values, values of the cost function $C_1$ represented by Equation (12a) and the cost function $C_2$ represented by Equation (12b) are both 0. Therefore, in this case, the value of the cost function Cost represented by Equation (11) is 0.

Step 6: Determine whether or not a prescribed termination condition is satisfied. Whether or not the termination condition is satisfied corresponds to whether or not the value of the non-negative cost function Cost is sufficiently close to 0 (in other words, with respect to a prescribed constant $\varepsilon$ (>0), whether the value of the non-negative cost function Cost is smaller than a or equal to or smaller than $\varepsilon$). For example, a termination condition may be adopted such that processing is terminated when the non-negative cost function Cost takes a value that is sufficiently close to 0. Alternatively, a termination condition may be adopted such that processing is terminated when either the non-negative cost function Cost takes a value that is sufficiently close to 0 or the number of iterations reaches a prescribed number of iterations. When the termination condition is satisfied, the center coordinates ($x_c$, $y_c$) and the deflection angle φ and/or the length $R_a$ of a major axis and the length $R_b$ of a minor axis are calculated using the hyperparameter α obtained in step 3 and output to terminate processing. The center coordinates ($x_e$, $y_e$), the deflection angle φ, the length $R_a$ of a major axis, and the length $R_b$ of a minor axis may be calculated according to Equations (2a), (2b), (3), and (4). When the termination condition is not satisfied, the tangent slopes $θ_1$ and $θ_2$ of the ellipse at the points P1 and P2 are updated and steps 2 to 5 are repeated.

Steps 1 to 6 can be executed using Newton's method or a gradient method. Newton's method is a method of obtaining, with respect to a function f(x), x such that f(x)=0, and the gradient method is a method of obtaining, with respect to a function f(x), x such that f(x) is minimized. Therefore, using Newton's method or the gradient method is to obtain, as optimum values, the tangent slopes $θ_1$ and $θ_2$ of the ellipse at the points P1 and P2 where the non-negative cost function Cost assumes a value that is sufficiently close to 0 (or assumes a minimum value).

Next, the eye rotation center coordinate calculation algorithm will be described.

<<Eye Rotation Center Coordinate Calculation Algorithm>>

Step 1: Provide a suitable initial value as the eye rotation center coordinates ($x_e$, $y_e$).

Step 2: Under the assumption that the eye rotation center coordinates are ($x_e$, $y_e$), obtain a time variation $P_{xy}(t)$ of an iris center position that indicates a position of a center of an ellipse representing an iris using the ellipse profile calculation algorithm. Specifically, first, with respect to a captured image of each row (pixel row), the ellipse profile calculation algorithm is applied and an ellipse profile of each row is estimated to obtain an iris center position of each row. By performing this processing with respect to all rows (all rows which include the iris) of the provided image, a series of iris center positions with respect to each row is obtained. This series will be referred to as the time variation $P_{xy}(t)$ of the iris center position.

Step 3: With respect to the time variation $P_{xy}(t)$ of the iris center position obtained in step S2, a parameter set is variously changed and fitted using a prescribed function $P_{xy,model}(t)$. Let $C_s$ denote a fitting cost value obtained as a result of the fitting. Specifically, the fitting processing is performed by an optimization approach (for example, Ceres solver) and the fitting cost value $C_s$ is obtained as, for example, a square error between $P_{xy}(t)$ and the optimized function $P_{xy,model}(t)$. It should be noted that, in order to avoid being trapped in a localized solution, the initial values of the parameter set are desirably provided in several patterns.

The prescribed function $P_{xy,model}(t)$ is a function that creates a model of eye movement and differs as follows between a case where a saccade has occurred and a case where a saccade has not occurred in the provided image.

(a) A Case of an Image in which a Saccade has Occurred

The prescribed function $P_{xy,model}(t)$ is represented when t>$t_0$ as

[Formula 16]

$$P_{xy,model}(t) = y'_0 + A\left\{1-e^{-\zeta\omega_n t}\left(\frac{\zeta}{\sqrt{1-\zeta^2}}\sin\omega_d(t-t_0) + \cos\omega_d(t-t_0)\right)\right\}$$

and represented when t<$t_0$ as

[Formula 17]

$$P_{xy,model}(t)=y_0'.$$

The equations given above are based on the fact that a time series of iris center positions in a time segment during which a saccade occurs can be modeled as a step response of a position control system. The parameter set to be an object of optimization is {A, ξ, $ω_n$, $t_0$, $y'_0$}. In this case, $y'_0$ represents an initial value of an iris center position, $t_0$ represents a start time point of a saccade, A represents an amplitude of the saccade, ξ represents a damping coefficient of the saccade, and $ω_n$ represents a natural angular frequency of the saccade, where t is an index representing time. The amplitude A is a movement amount when a movement of the eye due to the saccade converges. The natural angular frequency $ω_n$ corresponds to an index that represents a speed of a response of a saccade and the damping coefficient ξ corresponds to an index that represents convergence of the response of the saccade. It should be noted that $ω_d$ is a value which is determined from the damping coefficient and the natural angular frequency and which is expressed as follows.

[Formula 18]

$$ω_d=ω_n\sqrt{1-\zeta^2}$$

(b) A Case of an Image in which a Saccade has not Occurred

The prescribed function $P_{xy,model}(t)$ is represented as follows.

[Formula 19]

$$P_{xy,model}(t)=y_0'+Vt$$

where $y'_0$ represents an initial value of an iris center position and V represents an average speed (a trend) of the iris center position.

In this case, a method of determining whether or not a saccade has occurred in the provided image is as described below.

[Saccade Determination Method]

With respect to a plurality of images, iris center positions are calculated by, for example, simple ellipse fitting without taking the rolling shutter effect into consideration. The plurality of images used in this case include a prescribed image and are a set of a sufficient number of images. Next, a first-order difference sequence is calculated with respect to the time series of iris center positions obtained from the plurality of images, and an average value $m_s$ and a standard deviation $σ_s$ of the difference sequence are obtained. When a value $P_s$ of the first-order difference sequence that corresponds to the prescribed image satisfies

[Formula 20]

$$|P_s-m_s|>n_s\cdot\sigma_{s_i}$$

it is determined that a saccade had occurred during imaging of the prescribed image. In this case, $n_s$ is a constant for which a value of approximately 6 to 8 is desirably used in accordance with a level of noise contained in the acquired first-order difference sequence. When it is determined that the acquired information on iris center positions contains a large amount of noise or the like, a moving average deviation within a suitable range may be used when calculating the first-order difference sequence.

Step 4: When the fitting cost value $C_s$ is smaller than a prescribed threshold or equal to or smaller than the prescribed threshold, the eye rotation center coordinates $(x_e, y_e)$ at the present time point are output and processing is terminated. Otherwise, the eye rotation center coordinates $(x_e, y_e)$ are updated and processing of step 2 and thereafter is repeated.

Since the present invention is premised on the rolling shutter system, photography time points differ from one row of images to the next. In other words, since a time point at which a certain row is photographed differs from a time point at which a next row is photographed and a position of the iris fluctuates between the time points, it can be said that time-series data of the iris center positions that is obtained with respect to each row represents a temporal change (movement) of the iris center. In step 3, the time-series data of the iris center positions obtained in step 2 is fitted with a prescribed function. Therefore, step 4 may be described processing for determining reliability of the time-series data of the iris center positions (in other words, an estimation result of an ellipse profile). When accuracy of fitting performed using a function that models a movement of an eye (an iris) as the prescribed function is poor (when the fitting cost value is larger than a prescribed threshold), reliability of the estimation result of the time-series data of the iris center positions is conceivably low (not appropriate as a movement of an eye). Therefore, in this case, a return is made to step 2 once more and processing is performed once again from the estimation of the iris center position. On the other hand, when fitting accuracy is high (when the fitting cost value is smaller than the prescribed threshold), since reliability of the estimation result of the time-series data of the iris center positions is conceivably high (appropriate as a movement of an eye), the estimated eye rotation center coordinates $(x_e, y_e)$ are output as a final estimation result.

First Embodiment

Figure 4:
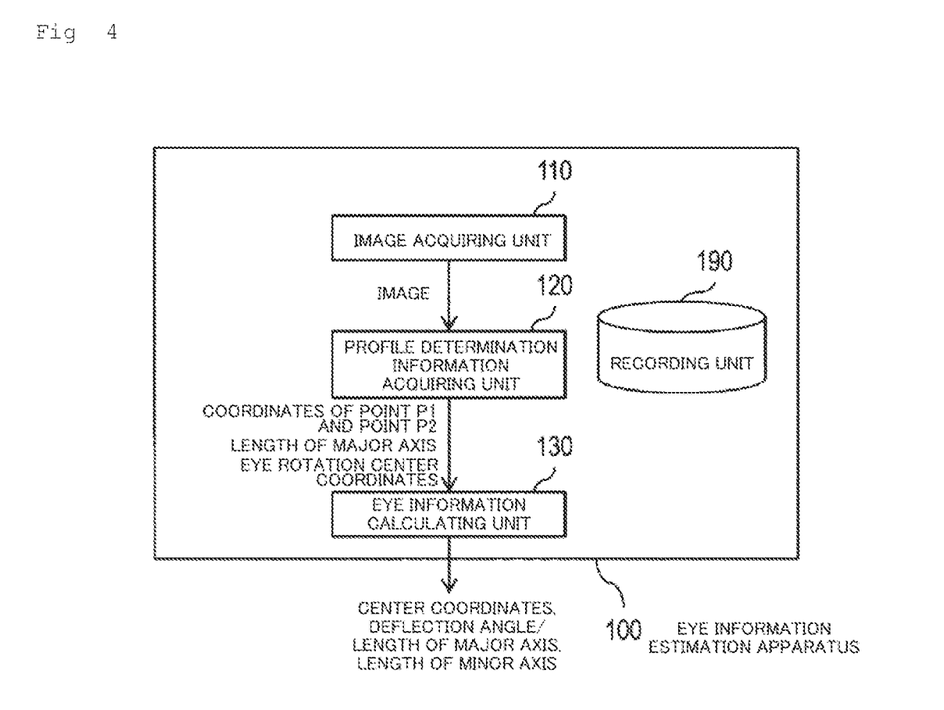
FIG. 4 is a block diagram showing an example of a configuration of an eye information estimation apparatus 100.
Figure 5:
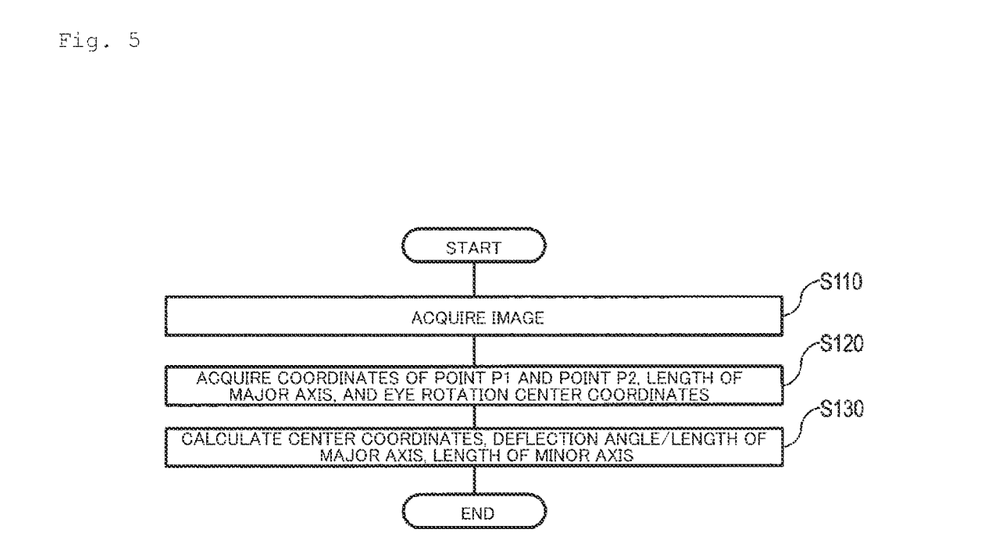
FIG. 5 is a flow chart showing an example of operations of the eye information estimation apparatus 100.

Hereinafter, an eye information estimation apparatus 100 will be described with reference to FIGS. 4 and 5. FIG. 4 is a block diagram showing a configuration of the eye information estimation apparatus 100. FIG. 5 is a flow chart showing operations of the eye information estimation apparatus 100. As shown in FIG. 4, the eye information estimation apparatus 100 includes an image acquiring unit 110, a profile determination information acquiring unit 120, an eye information calculating unit 130, and a recording unit 190. The recording unit 190 is a constituent unit that records information necessary for processing by the eye information estimation apparatus 100 when appropriate. For example, the recording unit 190 records the eye rotation radius $R_e$, acquired in advance.

Operations of the eye information estimation apparatus 100 will be described in accordance with FIG. 5.

[Image Acquiring Unit 110]

In S110, the image acquiring unit 110 acquires an image obtained by photographing an eye of a person who is a subject and outputs the image. While a camera with a relatively low sampling frequency such as a camera of a smartphone is assumed in this case as a camera to be used for image photography, a camera with a high sampling frequency may be used instead. The camera may be configured to photograph both left and right eyes or configured to photograph only one of the eyes. Hereinafter, it is assumed that the camera is configured to photograph only one eye.

[Profile Determination Information Acquiring Unit 120]

In S120, using the image acquired in S110 as an input, the profile determination information acquiring unit 120 acquires and outputs coordinates $(x_1, y_0)$ and $(x_2, y_0)$ of the two points P1 and P2, the length R, and the eye rotation center coordinates $(x_e, y_e)$. In this case, the two points P1 and P2 refer to two points that correspond to a limbus of a pupil or an iris in a prescribed row included in the image. In addition, the length R refers to, when a shape of the pupil or the iris is assumed to be an ellipse, a length of a major axis of the ellipse. Furthermore, the eye rotation center coordinates refers to eye rotation center coordinates of a three-dimensional eye rotation system to which the pupil or the iris is constrained. The method described in <Technical background> may be used as an acquisition method of the coordinates $(x_1, y_0)$ and $(x_2, y_0)$ of the points P1 and P2, the length R of the major axis, and the eye rotation center coordinates $(x_e, y_e)$). In this case, the profile determination information acquiring unit 120 is to acquire a value of the eye rotation center coordinates that is assumed in a situation such as the following as the eye rotation center coordinates $(x_e, y_e)$. "A situation such as the following" described above refers to a situation where the value of the eye rotation center coordinates is assumed to be a certain value and the series of the iris center position which is acquired in S110 and which is obtained for each row of the image becomes fittable at a prescribed accuracy with a prescribed function. The prescribed function in this case refers to a function that models a movement of an eye.

[Eye Information Calculating Unit 130]

In S130, the eye information calculating unit 130 uses the coordinates $(x_1, y_0)$ and $(x_2, y_0)$ of the points P1 and P2, the length R of the major axis, and the eye rotation center coordinates $(x_e, y_e)$ acquired in S120, the tangent slopes $\theta_1$ and $\theta_2$ of the ellipse at the points P1 and P2, and the eye rotation radius $R_e$ as input. In addition, the eye information calculating unit 130 calculates an ellipse profile including center coordinates $(x_c, y_c)$ and a deflection angle (of the ellipse that represent a position of a pupil or an iris and a length $R_a$ of a major axis and a length $R_b$ of a minor axis of the ellipse that represent a size of the pupil or the iris. Furthermore, the eye information calculating unit 130 outputs at least one profile among the ellipse profile. In this case, the tangent slopes $\theta_1$ and $\theta_2$ of the ellipse at the points P1 and P2 may be acquired from the image acquired in S110 by, for example, the method described in <Technical background>. In other words, the tangent slopes $\theta_1$ and $\theta_2$ are values calculated from coordinates of points corresponding to a limbus of the pupil or the iris of a row adjacent to the prescribed row and the coordinates $(x_1, y_0)$ and $(x_2, y_0)$ of the points P1 and P2. In this case, in S120, the profile determination information acquiring unit 120 may also acquire the tangent slopes $\theta_1$ and $\theta_2$ from the image acquired in step S110.

Figure 6:
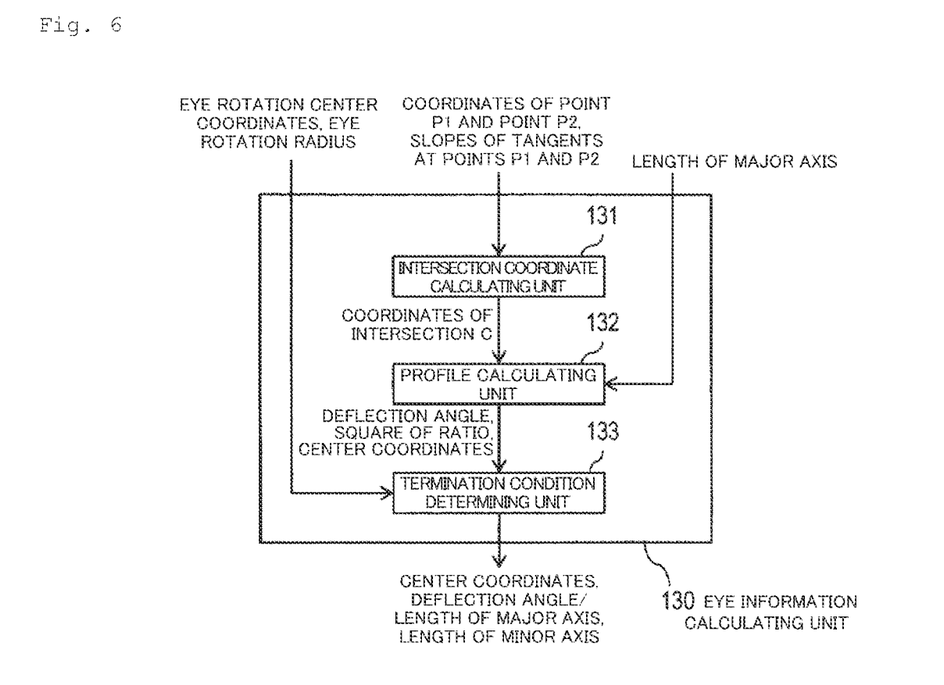
FIG. 6 is a block diagram showing an example of a configuration of an eye information calculating unit 130.
Figure 7:
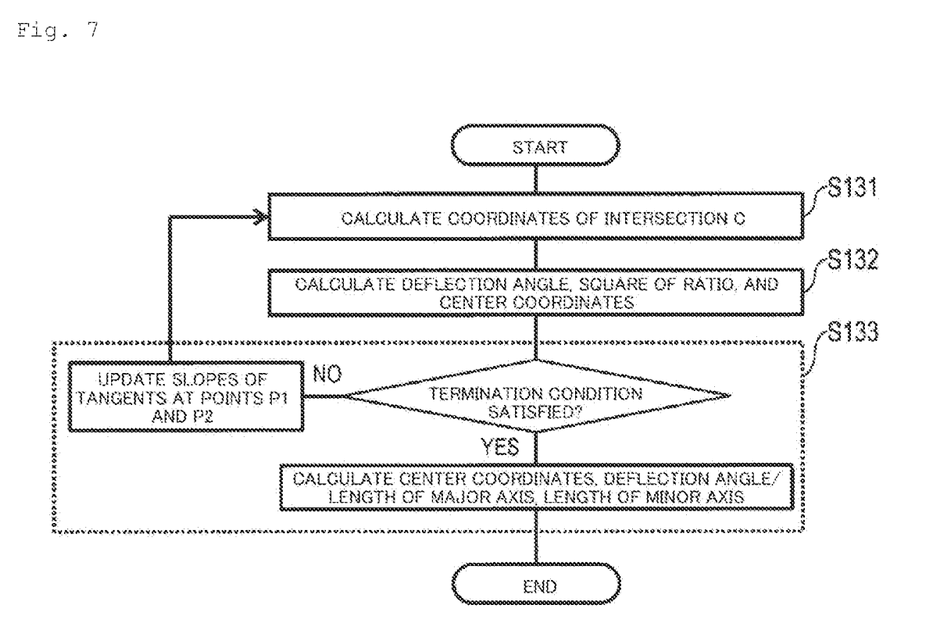
FIG. 7 is a flow chart showing an example of operations of the eye information calculating unit 130.

Hereinafter, the eye information calculating unit 130 will be described with reference to FIGS. 6 and 7. FIG. 6 is a block diagram showing a configuration of the eye information calculating unit 130. FIG. 7 is a flow chart showing operations of the eye information calculating unit 130. As shown in FIG. 6, the eye information calculating unit 130 includes an intersection coordinate calculating unit 131, a profile calculating unit 132, and a termination condition determining unit 133.

[Intersection Coordinate Calculating Unit 131]

In S131, the intersection coordinate calculating unit 131 calculates, from the coordinates $(x_1, y)$ and $(x_2, y_0)$ of the points P1 and P2 and the tangent slopes $\theta_1$ and $\theta_2$ of the ellipse at the points P1 and P2, coordinates $(x_s, y_s)$ of an intersection C of the tangents. Specifically, the coordinates $(x_s, y_s)$ of the intersection C are calculated according to Equation (1).

[Profile Calculating Unit 132]

In S132, the profile calculating unit 132 obtains the hyperparameter α (where |α|≤1) from the coordinates $(x_1, y_0)$ and $(x_2, y_0)$ of the points P1 and P2 and the coordinates $(x_s, y_s)$ of the intersection C having been calculated in S131, and the length R of the major axis. Accordingly, the profile calculating unit 132 calculates the deflection angle φ of the ellipse, a square $r^2$ of the ratio r of the length of the minor axis to the length of the major axis of the ellipse, and the center coordinates $(x_c, y_c)$ of the ellipse. Hereinafter, specific descriptions will be presented.

First, using the coordinates $(x_1, y_0)$ and $(x_2, y_0)$ of the points P1 and P2 and the coordinates $(x_s, y_s)$ of the intersection C, the profile calculating unit 132 obtains an expression of the length $R_a$ of the major axis using the hyperparameter α (in other words, Equation (4)).

Next, the profile calculating unit 132 determines the hyperparameter α using the expression of the length $R_a$ of the major axis in Equation (4) and the length R of the major axis. Specifically, α (where |α|≤1) is to be obtained such that the value of Equation (4) is R.

In addition, using α determined as described above, the profile calculating unit 132 respectively calculates the deflection angle φ and the square $r^2$ of the ratio r according to Equation (3) and Equation (8). Furthermore, using α determined as described above, the profile calculating unit 132 calculates the center coordinates $(x_c, y_c)$ according to Equation (2a) and Equation (2b).

[Termination Condition Determining Unit 133]

In S133, based on the deflection angle 9, the square $r^2$ of the ratio r, and the center coordinates $(x_c, y_c)$ of the ellipse calculated in S132, the eye rotation center coordinates $(x_e, y_e)$, and the eye rotation radius $R_e$, the termination condition determining unit 133 determines whether or not a prescribed termination condition is satisfied. When the termination condition is satisfied, the termination condition determining unit 133 outputs at least one profile among an ellipse profile which is calculated using the hyperparameter α determined in S132 and which includes the center coordinates $(x_c, y_c)$, the deflection angle φ, the length $R_a$ of the major axis, and the length $R_b$ of the minor axis of the ellipse. Otherwise, the tangent slopes $\theta_1$ and $\theta_2$ of the ellipse at the points P1 and P2 are updated according to a prescribed method (for example, Newton's method) and processing by the eye information calculating unit 130 is recursively executed using the updated tangent slopes $\theta_1$ and $\theta_2$. In other words, the eye information calculating unit 130 repeats the process of S131 and thereafter. In doing so, the eye information calculating unit 130 uses the values acquired in S120 with respect to the coordinates $(x_1, y_0)$ and $(x_2, y_0)$ of the points P1 and P2, the length R of the major axis, and the eye rotation center coordinates $(x_e, y_e)$ and uses the value recorded in the recording unit 190 with respect to the eye rotation radius $R_e$.

In this case, the termination condition described above is a condition which requires that, with respect to a prescribed constant ε (>0), the value of the non-negative cost function Cost be smaller than e or equal to or smaller than e and which is derived from the assumption related to the three-dimensional eye rotation system. The value of the non-negative cost function Cost is calculated according to Equation (11) using the deflection angle φ of the ellipse, the square $r^2$ of the ratio r of the length of the minor axis to the length of the major axis of the ellipse, and the center coordinates $(x_c, y_c)$ of the ellipse calculated in S132. More specifically, the value of the non-negative cost function Cost can be calculated according to Equation (11) using the deflection angle φ, the square $r^2$ of the ratio r, the center coordinates $(x_c, y_c)$, the eye rotation center coordinates $(x_e, y_e)$, and the eye rotation radius $R_e$.

The termination condition determining unit 133 may calculate the center coordinates $(x_c, y_c)$ and the deflection angle φ of the ellipse according to Equations (2a), (2b), and (3) using the hyperparameter α determined as described above. In addition, the termination condition determining unit 133 may calculate the length $R_a$ of the major axis and the length $R_b$ of the minor axis of the ellipse according to Equation (4) using the hyperparameter α determined as described above.

As described above, using the eye rotation center coordinates $(x_e, y_e)$, the eye rotation radius $R_e$, and the ellipse profile, the eye information calculating unit 130 calculates the value of the non-negative cost function Cost which represents validity of the ellipse profile. In addition, the eye information calculating unit 130 calculates the ellipse profile when the value of the non-negative cost function Cost satisfies a prescribed condition as an ellipse profile to be an output object.

When using an image obtained by photographing both left and right eyes, the processing of S120 to S130 may be executed with respect to each eye.

According to the invention described in the present embodiment, information on a position and a size of a pupil or an iris can be estimated, using an image photographed by a camera with a low sampling frequency, in time units that are finer than the actual sampling frequency.

<Addendum>

For example, as a single hardware entity, the apparatus according to the present invention has: an input unit to which a keyboard or the like can be connected; an output unit to which a liquid crystal display or the like can be connected; a communication unit to which a communication apparatus (such as a communication cable) that is capable of communicating with the outside of the hardware entity can be connected; a CPU (Central Processing Unit which may be provided with a cache memory, a register, or the like); a RAM and a ROM that are memories; an external storage apparatus that is a hard disk; and a bus that connects the input unit, the output unit, the communication unit, the CPU, the RAM, the ROM, and the external storage apparatus so as to be capable of exchanging data. In addition, the hardware entity may be provided with an apparatus (a drive) that is capable of reading from and writing into a recording medium such as a CD-ROM. Examples of a physical entity provided with such a hardware resource include a general-purpose computer.

The external storage apparatus of the hardware entity stores programs necessary for realizing the functions described above, data required during processing of the programs, and the like (besides the external storage apparatus, for example, the programs may be stored in a ROM that is a read-only storage apparatus). In addition, data or the like obtained by the processing of the programs is appropriately stored in the RAM, the external storage apparatus, or the like.

In the hardware entity, each program and data necessary for processing of the program which are stored in the external storage apparatus (or the ROM or the like) are loaded to a memory when necessary to be appropriately interpreted, executed, and processed by the CPU. As a result, the CPU realizes a prescribed function (each component represented as a unit, means, or the like in the description presented above).

The present invention is not limited to the embodiment described above and various modifications can be made without departing from the spirit and scope of the present invention. In addition, the various types of processing explained in the embodiment described above may not only be executed in chronological order according to the descriptions but may also be executed in parallel or on an individual basis in accordance with processing capabilities of an apparatus to be used to execute the processing or as may be necessary.

As already described, when realizing the processing functions of the hardware entity (the apparatus according to the present invention) explained in the embodiment described above with a computer, processing contents of functions which the hardware entity must be equipped with are described by a program. In addition, the processing functions of the hardware entity described above are realized on the computer by having the computer execute the program.

The program describing the processing contents can be recorded in a computer-readable recording medium. Any computer-readable recording medium may be used such as a magnetic recording apparatus, an optical disk, a magneto-optical recording medium, and a semiconductor memory. Specifically, for example, a hard disk apparatus, a flexible disk, a magnetic tape, or the like can be used as a magnetic recording apparatus, a DVD (Digital Versatile Disc), a DVD-RAM (Random Access Memory), a CD-ROM (Compact Disc Read Only Memory), a CD-R (Recordable)/RW (ReWritable) or the like can be used as an optical disk, an MO (Magneto-Optical disc) or the like can be used as a magneto optical recording medium, and an EEP-ROM (Electronically Erasable and Programmable-Read Only Memory) or the like can be used as a semiconductor memory.

In addition, the program is distributed by, for example, selling, transferring, or lending a portable recording medium such as a DVD or a CD-ROM on which the program is recorded. Furthermore, a configuration may be adopted in which the program is stored in a storage apparatus of a server computer and the server computer transmits the program to other computers via network in order to distribute the program.

For example, a computer that executes such a program first temporarily stores the program recorded in a portable recording medium or the program transmitted from a server computer in its own storage apparatus. In addition, when executing processing, the computer reads the program stored in its own storage apparatus and executes processing in accordance with the read program. Furthermore, as an alternative execution mode of the program, a computer may read a program directly from a portable recording medium and execute processing in accordance with the program or, every time the program is transmitted from a server computer to the computer, the computer may sequentially execute processing in accordance with the received program. In addition, a configuration may be adopted in which a program is not transmitted to the computer from a server computer and the processing described above is executed by a so-called ASP (Application Service Provider) type service which realizes a processing function only by issuing an execution instruction and acquiring a result thereof. It should be noted that the program according to the present embodiment includes information which is to be processed by an electronic computer and which is equivalent to a program (data or the like which is not a direct command intended for a computer but which has a property of specifying processing by the computer).

In addition, in the embodiment, while the hardware entity is configured by having a computer execute a prescribed program, at least a part of processing contents thereof may be realized by hardware.

The invention claimed is:

1. An eye information estimation apparatus, comprising:
a profile determination information acquirer configured to acquire, from an image obtained by photographing an eye of a person who is a subject, coordinates $(x_1, y_0)$ and $(x_2, y_0)$ of two points $P_1$ and $P_2$ corresponding to a limbus of a pupil or an iris of a prescribed row included in the image and, when a shape of the pupil or the iris is assumed to be an ellipse, a length R of a major axis of the ellipse and eye rotation center coordinates $(x_e, y_e)$ of a three-dimensional eye rotation system that constrains the pupil or the iris; and
an eye information determiner configured to determine, when $\theta_1$ and $\theta_2$ respectively denote tangent slopes of the ellipse at the point $P_1$ and the point $P_2$ and Re denotes an eye rotation radius of the three-dimensional eye rotation system, an ellipse profile including center coordinates $(x_c, y_c)$ and a deflection angle $\varphi$ of the ellipse that represent a position of the pupil or the iris and a length Ra of a major axis and a length $R_b$ of a minor axis of the ellipse that represent a size of the pupil or the iris from the coordinates $(x_1, y_0)$ and $(x_2, y_0)$ of the points $P_1$ and $P_2$, the tangent slopes $\theta_1$ and $\theta_2$, the length R of the major axis, the eye rotation center coordinates $(x_e, y_e)$, and the eye rotation radius $R_e$.

2. The eye information estimation apparatus according to claim 1, wherein the eye information determiner determines a value of a non-negative cost function Cost which represents validity of an ellipse profile using the eye rotation center coordinates $(x_e, y_e)$, the eye rotation radius $R_e$, and the ellipse profile, and determines the ellipse profile when the value of the non-negative cost function Cost satisfies a prescribed condition as the ellipse profile.

3. The eye information estimation apparatus according to claim 2, wherein the profile determination information acquirer acquires, as the eye rotation center coordinates $(x_e, y_e)$, the value of the eye rotation center coordinates when a series of iris center positions which is obtained for each row of the image by assuming a certain value of the eye rotation center coordinates becomes fittable at a prescribed accuracy with a prescribed function that models movement of an eye.

4. The eye information estimation apparatus according to claim 2, wherein the eye information determiner determines the ellipse profile using one of the Newton's method or a gradient method to optimize the non-negative cost function assumes a value that is sufficiently close to zero or a minimum value.

5. The eye information estimation apparatus according to claim 2, wherein the eye information determiner determines the ellipse profile based on a time interval that is less than a sampling interval of the image.

6. The eye information estimation apparatus according to claim 5, wherein a sampling rate of the image is less than 1000 Hz.

7. The eye information estimation apparatus according to claim 1, wherein the tangent slopes $\theta_1$ and $\theta_2$ are values calculated from coordinates of points corresponding to a limbus of a pupil or an iris of a row adjacent to the prescribed row and the coordinates $(x_1, y_2)$ and $(x_2, y_0)$ of the points P1 and P2.

8. An eye information estimation method, comprising:
acquiring, by a profile determination information acquirer of an eye information estimation apparatus, from an image obtained by photographing an eye of a person who is a subject, coordinates $(x_1, y_2)$ and $(x_2, y_0)$ of two points P1 and P2 corresponding to a limbus of a pupil or an iris of a prescribed row included in the image and, when a shape of the pupil or the iris is assumed to be an ellipse, a length R of a major axis of the ellipse and eye rotation center coordinates $(x_e, y_e)$ of a three-dimensional eye rotation system that constrains the pupil or the iris; and
determining, by an eye information determiner of the eye information estimation apparatus, when $\theta_1$ and $\theta 2$ denote tangent slopes of the ellipse at the point P1 and the point P2 and $R_e$ denotes an eye rotation radius of the three-dimensional eye rotation system, an ellipse profile including center coordinates $(x_c, y_c)$ and a deflection angle $\theta$ of the ellipse that represent a position of the pupil or the iris and a length $R_a$ of a major axis and a length $R_b$ of a minor axis of the ellipse that represent a size of the pupil or the iris from the coordinates $(x_1, y_0)$ and $(x_2, y_0)$ of the points P1 and P2, the tangent slopes $\theta_1$ and $\theta_2$, the length R of the major axis, the eye rotation center coordinates $(x_e, y_e)$, and the eye rotation radius $R_e$.

9. The eye information estimation method according to claim 8, wherein the eye information determiner determines a value of a non-negative cost function Cost which represents validity of an ellipse profile using the eye rotation center coordinates $(x_e, y_e)$, the eye rotation radius $R_e$, and the ellipse profile, and determines the ellipse profile when the value of the non-negative cost function Cost satisfies a prescribed condition as the ellipse profile.

10. The eye information estimation method according to claim 9, wherein the profile determination information acquirer acquires, as the eye rotation center coordinates $(x_e, y_e)$, the value of the eye rotation center coordinates when a series of iris center positions which is obtained for each row of the image by assuming a certain value of the eye rotation center coordinates becomes fittable at a prescribed accuracy with a prescribed function that models movement of an eye.

11. The eye information estimation method according to claim 8, wherein the tangent slopes $\theta_1$ and $\theta_2$ are values calculated from coordinates of points corresponding to a limbus of a pupil or an iris of a row adjacent to the prescribed row and the coordinates $(x_1, y_0)$ and $(x_2, y_0)$ of the points P1 and P2.

12. The eye information estimation method according to claim 9, wherein the eye information determiner determines the ellipse profile using one of the Newton's method or a gradient method to optimize the non-negative cost function assumes a value that is sufficiently close to zero or a minimum value.

13. The eye information estimation method according to claim 9, wherein the eye information determiner determines the ellipse profile based on a time interval that is less than a sampling interval of the image.

14. The eye information estimation method according to claim 13, wherein a sampling rate of the image is less than 1000 Hz.

15. A computer-readable non-transitory recording medium storing a computer-executable program instructions that when executed by a processor cause a computer system to:
acquire, by a profile determination information acquirer of an eye information estimation apparatus, from an image obtained by photographing an eye of a person who is a subject, coordinates $(x_1, y_2)$ and $(x_2, y_0)$ of two points $P_1$ and $P_2$ corresponding to a limbus of a pupil or an iris of a prescribed row included in the image and, when a shape of the pupil or the iris is assumed to be an ellipse, a length R of a major axis of the ellipse and eye rotation center coordinates $(x_e, y_e)$ of a three-dimensional eye rotation system that constrains the pupil or the iris; and
determine, by an eye information determiner of the eye information estimation apparatus, when $\theta_1$ and $\theta_2$ denote tangent slopes of the ellipse at the point P1 and the point P2 and $R_e$ denotes an eye rotation radius of the three-dimensional eye rotation system, an ellipse profile including center coordinates $(x_c, y_c)$ and a deflection angle $\varphi$ of the ellipse that represent a position of the pupil or the iris and a length $R_a$ of a major axis and a length $R_b$ of a minor axis of the ellipse that represent a size of the pupil or the iris from the coordinates $(x_1, y_0)$ and $(x_2, y_0)$ of the points P1 and P2, the tangent slopes $\theta_1$ and $\theta_2$, the length R of the major axis, the eye rotation center coordinates $(x_e, y_e)$, and the eye rotation radius $R_e$.

16. The computer-readable non-transitory recording medium of claim 15, wherein the eye information determiner determines a value of a non-negative cost function Cost which represents validity of an ellipse profile using the eye rotation center coordinates $(x_e, y_e)$, the eye rotation radius $R_e$, and the ellipse profile, and determines the ellipse profile when the value of the non-negative cost function Cost satisfies a prescribed condition as the ellipse profile.

17. The computer-readable non-transitory recording medium of claim 16, wherein the profile determination information acquirer acquires, as the eye rotation center coordinates $(x_e, y_e)$, the value of the eye rotation center coordinates when a series of iris center positions which is obtained for each row of the image by assuming a certain value of the eye rotation center coordinates becomes fittable at a prescribed accuracy with a prescribed function that models movement of an eye.

18. The computer-readable non-transitory recording medium of claim 16, wherein the eye information determiner determines the ellipse profile using one of the Newton's method or a gradient method to optimize the non-negative cost function assumes a value that is sufficiently close to zero or a minimum value.

19. The computer-readable non-transitory recording medium of claim 16, wherein the eye information determiner determines the ellipse profile in a time interval that is less than a sampling interval of the image.

20. The computer-readable non-transitory recording medium of claim 15, wherein the tangent slopes $\theta_1$ and $\theta_2$ are values calculated from coordinates of points corresponding to a limbus of a pupil or an iris of a row adjacent to the prescribed row and the coordinates $(x_1, y_0)$ and $(x_2, y_0)$ of the points P1 and P2.

* * * * *